United States Patent [19]

Akerman et al.

[11] 4,008,335

[45] Feb. 15, 1977

[54] METHOD OF TREATING BAKER'S YEAST

[75] Inventors: Emanuel Akerman, Bronx, N.Y.; Seymour Pomper, Stamford, Conn.

[73] Assignee: Standard Brands Incorporated, New York, N.Y.

[22] Filed: Nov. 3, 1975

[21] Appl. No.: 628,038

[52] U.S. Cl. .................................. 426/62; 195/98
[51] Int. Cl.² ........................................ C12C 11/16
[58] Field of Search ................ 426/61, 62; 195/98

[56] References Cited
FOREIGN PATENTS OR APPLICATIONS 1,246,231   9/1971   United Kingdom ................ 426/62

OTHER PUBLICATIONS

Holderby, J. W., Fiat Final Report No. 619, May 22, 1946, Field Information Agency, Technical.

*Primary Examiner*—Raymond N. Jones

[57] ABSTRACT

An aqueous suspension of yeast is treated with a sufficient amount of an acid to achieve a pH within the range of from about 0.9 to about 2.0 under conditions whereby the initial leavening activity of the yeast in sweet dough is not detrimentally affected. The yeast suspension is then treated with a neutralizing agent to raise the pH of the suspension to within the range of from about 2.5 to about 6, the major portion of the neutralizing agent being composed of a material which is a source of ammonium ions.

9 Claims, No Drawings

METHOD OF TREATING BAKER'S YEAST

THE INVENTION

This invention relates to a method of treating yeast. More particularly, this invention relates to a method of improving the filterability, rehydratability and storage stability of acid treated yeast.

The largest use for viable yeast is for baking purposes. Yeast is supplied to bakeries and to consumers for baking in two forms, i.e., active dry and compressed. The species of yeast used for baking purposes is generally *Saccharomyces cerevisiae*. There are many strains of yeast which are included within this species and the particular strain used depends on many factors. One factor is whether a compressed yeast or active dry yeast is to be produced.

Strains of baker's yeast can be generally grouped into two broad categories when classified according to the bios response procedure published by Schultz and Atkin in *Archives of Biochemistry*, Vol. 14, p. 369 (August 1947). The first group is classified as Bios No. 236. Yeast in this group is generally used when it is desirable to produce a compressed yeast. The second group is classified as Bios No. 23, and is typically used when an active dry yeast is to be produced. Although yeast of the Bios No. 23 group can be propagated to higher yields, and is hardier and metabolically more stable than yeast of the Bios No. 236 group, yeast of the latter group is preferred by commercial bakers because of its superior leavening activity.

Active dry yeast is a yeast composition containing up to 10 percent moisture, and generally from 5 to 8 percent moisture. Yeast of the Bios No. 23 group is usually selected for the production of active dry yeast because, as mentioned above, it is hardier and metabolically more stable than Bios No. 236, and accordingly can be dried to low moisture levels with minimal loss of its initial leavening activity occurring. In some instances, yeast of the Bios NO. 236 group can be used to prepare an active dry yeast product.

Yeast which is to be used for baking purposes is produced on a commercial scale by a multi-stabe operation. This multi-stage operation includes, generally, a first step of preparing the basic ingredients needed by the yeast for growth. The basic ingredients may include sterilized cane sugar and/or molasses, corn steep liquor and an acid or alkali to adjust the pH of the mixture to the range of 4 to 5. The mixture is diluted with water, fortified by the addition of inorganic nitrogen and phosphorus-containing compounds and, when necessary, the pH of the mixture is again adjusted to a range of 4 to 5. This mixture is known in the art as "mash".

To attain the high degree of purity required for yeast which is to be used for baking purposes and for other reasons, yeast is grown in stages, starting with seed stages and finishing with growing in fermentors of commercial scale. The yeast is grown under aerobic conditions by the addition of large volumes of air to the growth medium. Carbohydrates and nitrogen sources are continuously incorporated into the mash in the last stages of propagation. The temperature of the growth media is maintained in the range where optimum growth of the yeast occurs. After the propagation of the yeast, the yeast is separated from the other constituents of the growth media by centrifugation, washed and again centrifuged. Yeast at this stage is known in the art as cream yeast. Cream yeast is transferred to a filter where relatively large quantities of its extracellular water are removed. Yeast at this stage is known in the art as compressed yeast and contains approximately 30 percent yeast solids. Generally, this is the form of yeast that is supplied to commercial bakeries. Active dry yeast may be produced from a suitable compressed yeast by any of the several processes known in the art; for example, a process known as the "spaghetti process" which involves extruding compressed yeast in spaghetti form and drying it under controlled conditions on a moving belt.

Because of the manner in which yeast is grown, it frequently contains numerous common and, for the most part, harmless bacteria; however, it is generally considered to be desirable to maintain the number of the bacteria at the lowest practicable level. For example, because of the relatively large air supply needed to grow the yeast under aerobic conditions, bacteria may be introduced with the air even though it is filtered. Furthermore, even though the apparatus used for growing the yeast is kept scrupulously clean and is sterilized on a regular basis, it is practically impossible to predict with any real degree of certainty that bacteria will not become mixed with the yeast during the propagation or handling thereof. This is principally because the conditions under which yeast is grown, i.e., pH, temperature, nutrients, etc., are at times conducive to growth of bacteria. Furthermore, yeast itself may serve as a nutrient for contaminating bacteria. Once the yeast does become infected with bacteria, the further growth of bacteria may be rapid.

There are numerous literature references which deal with bacterial infections of yeast. For instance, in the book entitled *Bakery Technology and Engineering* by Matz (The Avi Publishing Company, Inc., Westport, Conn., 1960) on page 62 it is disclosed that the bacterial content of yeast varies widely but generally it contains less than 500 million per wet gram of yeast. In the book entitled *Yeast Technology* by White (John Wiley and Sons, Inc., New York, New York, 1954) on page 238 it is disclosed that in a typical biological assay of yeast, the total bacteria count may be 25 million per gram. Considerable effort has been spent in the past to lower the bacterial content of yeast. However, yeast, because it must be in a viable and highly active state for baking, does not lend itself to normal pasteurization techniques such as heat, ultrafiltration, irradiation and the like since these techniques, generally, will not only destroy the bacteria present but will also destroy or harm the yeast.

British Pat. No. 1,246,231 discloses a method for treating yeast with an acid to affect pasteurization of the yeast without significantly reducing the viability of the yeast. It is also disclosed in the British patent that acid treatment of yeast under particular conditions will improve certain of the functional properties of yeast such as its initial leavening activity, cold water tolerance, storage stability, etc. The acid treatment is generally performed while the yeast is in aqueous suspension for the reasons that the acid should be distributed essentially evenly throughout the suspension of yeast cells so that there is no localized region of very high acidity which might detrimentally affect the leavening activity of the yeast and because it is common practice to perform the acid treatment at a point in the production of baker's yeast before the yeast is subjected to a filtration treatment.

Following the acid treatment, it is taught in the British Patent that the pH of the suspension is adjusted upwardly by the utilization of an alkali such as NaOH or $Na_2CO_3$ and the like.

The method taught by the British patent has not proven to be completely satisfactory in commercial use. One of the problems encountered in such use is that the acid treated and neutralized yeast suspension is difficult to filter. As a result, undesirably long periods are required to filter the suspension and thus necessitate increased expenditures for personnel and equipment which add to the cost of the final product. Moreover, in some instances, active dry yeast prepared from acid treated yeast does not rehydrate satisfactorily. Rehydration of active dry yeast, prior to its being utilized for baking purposes, is generally necessary if the yeast particles are relatively large since, otherwise, their effect on dough will not be constant throughout.

Generally, the lower the moisture content of active dry yeast, the greater is its storage stability. However, as yeast is dried, it gradually loses activity and, therefore, yeast is usually dried to an intermediate moisture content so that although it does not possess optimum storage stability or activity, it has these characteristics at a satisfactory commercial level. Surfactants and antioxidants have been incorporated into active dry yeast to improve the storage stability of yeast and its drying tolerance.

It is an object of the present invention to provide a method of improving the filterability of an aqueous suspension of yeast cells which have been acid treated.

It is still another object of the present invention to provide a method of improving the drying tolerance of yeast cells which have been acid treated.

It is another object of the present invention to improve the storage stability of active dry yeast made from yeast which has been acid treated.

It is yet another object of the present invention to improve the rehydratability of active dry yeast made from yeast which has been acid treated.

The attainment of one or more of the aforementioned objects in accordance with the present invention depends upon the particular embodiment of the invention practiced. Broadly, the present invention comprises acid treating an aqueous suspension of yeast to a pH within the range of from about 0.9 to about 2.0 under conditions whereby the initial leavening activity of the yeast in sweet dough is not detrimentally affected and then treating the acidified aqueous suspension with a neutralizing agent to raise the pH of the suspension to within the range of from about 2.5 to about 6, the major portion of the neutralizing agent being composed of a material which is a source of ammonium ions.

While a number of neutralizing agents which provide ammonium ions may be utilized in the present process, the preferred agents are $NH_3$, $NH_4OH$ and $NH_4HCO_3$ for economic reasons and ease of handling.

Although we do not wish to be bound to any theory or reason why the aforementioned advantages are achieved by using a source of ammonium ions for neutralizing acid treated yeast, it is believed that a complex mechanism is involved whereby the yeast cell wall is modified so that liquid can readily be removed from the cell and absorbed thereinto. This is manifested by the ability of the yeast treated according to the present process to be more readily filtered and, when dried, to be more readily rehydrated as compared to acid treated yeast which has been neutralized with NaOH, for example. Also, since moisture can be readily removed from the treated yeast, it can be dried to lower moisture levels without the addition of surfactants or antioxidants and without incurring a significant loss in leavening activity. Generally, as explained previously, the lower the moisture level of the yeast, the greater is its storage stability.

Typically, the acids used to treat the yeast will be hydrochloric, nitric and phosphoric. Generally, the yeast suspension will be treated with a sufficient amount of acid to lower the pH of the yeast to within a range of from about 0.9 to about 2.0 and preferably to a pH within a range of from about 1.1 to about 1.5.

The period and temperature of the acid treatment are interdependent variables and, generally, the higher the temperature, the shorter the period required for the acid treatment. Temperatures ranging from the freezing point of the yeast suspension to about 120° F may be utilized although the preferred temperature is from about 40° to about 60° F. Periods of from about 5 seconds to about 180 minutes are contemplated with the preferred period being from about 30 to about 60 minutes.

The pH to which the acidified yeast suspension is neutralized may also vary over a relatively wide range, i.e., from about 2.5 to about 6 but the preferred pH is in the range of from about 3.5 to about 4.5.

While it is contemplated that in the commercial utilization of the present process, the neutralizing agent will consist essentially of a source of ammonium ions, it should be distinctly understood that such neutralization agents may be utilized in combination with other neutralizing agents such as NaOH, $Na_2CO_3$ and the like so long as the amount of ammonium ions produced is sufficient to achieve one or more of the above enumerated benefits, i.e., improved filterability, rehydratability, storage stability, or drying tolerance.

Various test methods and terms used herein are defined as follows:

Rehydratability

The term rehydratability as used herein refers to the ability of the dried yeast cells to take up or absorb water and is determined as follows:

7.5 grams of dried yeast is suspended in water containing a suitable colorant, e.g., methylene blue dye, in a vessel with glass sides at a temperature of 100° F and stirred mechanically at 300 rpm. for a period of 90 seconds. The suspension is then observed for unrehydrated yeast cells which settle to the bottom of the vessel. If appreciable settling is observed, the suspension is periodically stirred and observed until substantially no yeast cells settle out of the suspension. The total of the combined stirring times is taken as a measure of the rehydratability of the yeast, the smaller the total, the more rehydratable being the yeast.

Leavening Activity

The leavening activity of the yeast samples was determined by means of sweet dough punch tests. This means of evaluating the leavening activity of yeast is well known in the art and involves preparing a sweet dough having present a known quantity of yeast, allowing it to rise to a predetermined volume, punching the dough down, allowing it to rise again to the same volume, punching it down and again allowing it to rise to the predetermined volume. The time required for the sweet dough to rise to the predetermined volume is measured and indicates the activity of the yeast—the shorter the required time, the better the activity of the yeast.

The term "initial leavening activity," as used herein, refers to the ability of freshly treated yeast to leaven sweet dough, as shown above, prior to the yeast's being stored.

The term "sweet dough," as used herein, refers to a dough formula containing from 15 to 25 percent, and preferably about 20 percent, sucrose by weight of the flour present.

In order to more clearly describe the nature of the present invention, specific Examples will hereinafter be described. It should be understood, however, that this is done solely by way of example and is intended neither to delineate the scope of the invention nor limit the ambit of the appended claims. In the Examples and through the specification, percentages refer to percent by weight unless otherwise specified.

EXAMPLE I

This Example illustrates the effect of treating an aqueous suspension of acid-treated yeast with a source of ammonium ions on the filterability of the suspension.

Cream yeast of the Bios 236 type having a solids content of 18 percent was cooled to a temperature of 40° F and a sufficient amount of 32 percent HCl diluted 1:2 with water was added with stirring to lower the pH of the suspension to about 1.3.

Samples of the acid treated yeast suspension were treated as follows:
1. neutralized with a 20 percent solution of $Na_2CO_3$ to a pH of 5.0
2. neutralized with a 20 percent solution of $NH_4HCO_3$ to a pH of 4.8
3. neutralized with a 14.5 percent $NH_4OH$ solution (29 percent $NH_3$ solution diluted 1:1 with water) to a pH of 5.0

Into an 11.5 cm Buchner funnel set in a vacuum flask was placed a wetted 11 cm Whatman No. 1 circular filter paper which had been precoated with starch. The starch coating was prepared by suspending 20 g of potato starch in 2 liters of water at room temperature. Exactly 200 ml of the well-shaken starch suspension was poured onto the filter paper in the funnel under vacuum and the vacuum maintained until water ceased to flow from the funnel.

Exactly 100 ml of each of the samples was quickly poured into funnels prepared as described above which were maintained under a vacuum of from 690 to 710 mm of mercury. The filtrates were collected in 50 ml graduated cylinders which had been set into the filter flasks. At various filtration time intervals, the amounts of filtrates collected were noted and are set forth in Table I below. Data were obtained on freshly prepared samples and, in some cases, on treated samples which had been stored at 40° F for 24 and 48 hours prior to filtering the same.

TABLE I

EFFECT OF NEUTRALIZING AGENTS ON FILTERABILITY OF ACID-TREATED YEAST

FILTRATE VOLUME - ml

| | | | | Pasteurized Yeast Samples | | | | |
|---|---|---|---|---|---|---|---|---|
| | | | | Neutralized with $Na_2CO_3$ | | Neutralized with $NH_4HCO_3$ | | Neutralized with $NH_4OH$ |
| Time Min. | Control (no treatment) Storage period, hrs.* | | | Storage period, hrs.* | | Storage period, hrs.* | | Storage period, hrs.* |
| | 0 | 24 | 48 | 0 | 48 | 0 | 48 | 0 |
| 0.5 | 8.8 | 8.8 | 9.5 | 7.5 | 5.0 | 8.0 | 7.0 | 7.5 |
| 1.0 | 15.9 | 15.8 | 16.0 | 12.5 | 11.3 | 14.8 | 13.5 | 13.8 |
| 1.5 | 21.7 | 21.8 | 22.0 | 17.5 | 15.5 | 20.8 | 18.5 | 18.8 |
| 2.0 | 26.7 | 26.5 | 26.8 | 21.8 | 20.5 | 26.0 | 22.0 | 23.5 |
| 2.5 | 31.0 | 31.0 | 31.3 | 26.0 | 24.0 | 30.5 | 27.0 | 27.5 |
| 3.0 | 35.5 | 34.9 | 35.3 | 29.4 | 27.5 | 34.7 | 30.3 | 31.5 |
| 3.5 | 39.8 | 39.2 | 39.3 | 33.6 | 31.0 | 38.6 | 33.5 | 35.3 |
| 4.0 | 43.2 | 42.2 | 42.8 | 36.8 | 33.6 | 41.5 | 36.7 | 38.3 |
| 4.5 | 45.5 | 44.3 | 45.0 | 39.4 | 36.6 | 44.2 | 39.2 | 42.0 |
| 5.0 | 47.3 | 46.1 | 46.9 | 42.0 | 39.9 | 45.9 | 41.2 | 43.0 |
| 6.0 | 49.7 | 48.5 | 49.6 | 45.3 | 42.5 | 48.5 | 44.2 | 45.9 |
| 7.0 | 51.2 | 50.0 | 51.0 | 47.6 | 45.0 | 51.0 | 46.5 | 48.7 |
| 8.0 | 52.0 | 51.5 | 52.0 | 49.2 | 47.5 | 52.0 | | |
| 9.0 | | | | 51.5 | 48.7 | | | |
| 10.0 | | | | | 49.8 | | | |
| Total | 53.0 | 53.0 | 53.0 | 52.0 | 52.0 | 52.5 | 52.0 | 51.5 |

*prior to filtering

As shown in the above Table, the use of a source of ammonium ions as neutralizing agent in an aqueous suspension of acid treated yeast provides improved filterability of the suspension as compared to the use of sodium carbonate as neutralizing agent.

EXAMPLE II

This Example illustrates the effect of treating an aqueous suspension of acid treated yeast with various neutralizing agents on the leavening activity of active dry yeast prepared from such yeast and on the rehydratability of the active dry yeast.

Cream yeast of the Bios 23 type having a solids content of 18 percent was acid treated and neutralized with $NH_4OH$ and $NH_4HCO_3$ as shown in the above Example. For comparison purposes, a sample of acid treated yeast was neutralized to a pH of 4.5 with a 25 percent solution of NaOH.

The cream yeast samples were filtered in a conventional manner to provide yeast cakes having a solids content of about 30 percent. A portion of each cake was extruded in spaghetti form and dried in air at a temperature in the range of from about 95° to about 120° F at relative humidities ranging from about 70 to about 10 percent. The initial leavening activity after storage of the active dry yeast samples is shown in Table II below. Also shown in the table are rehydratability data for the active dry yeast samples.

TABLE II

EFFECT OF NEUTRALIZING AGENTS ON REHYDRATABILITY AND LEAVENING ACTIVITY OF ACTIVE DRY YEAST PREPARED FROM ACID TREATED YEAST

| Neutralizing Agent: | Rehydratability (seconds) | Moisture (percent) | Leavening Activity in Sweet Dough Rise Time (Minutes) | |
|---|---|---|---|---|
| | | | Initial | After Storage* |
| Sodium Hydroxide | — | 7.8 | 60-37-37 | 75-50-51 |
| Sodium Hydroxide | — | 6.6 | 75-49-47 | 82-51-48 |
| Sodium Hydroxide | 250 | 7.8 | 60-36-33 | 76-58-57 |
| Ammonium Hydroxide | 140 | 6.8 | 60-37-40 | 71-47-49 |
| Ammonium Bicarbonate | 150 | 6.6 | 61-38-39 | 70-46-43 |

*Stored for 4 days at 115° F in air

As shown in Table II, active dry yeast prepared from a suspension of acid treated yeast which had been neutralized with a source of ammonium ions, as compared to sodium hydroxide, had improved rehydratability and could be dried to lower moisture levels without loss of leavening activity.

The terms and expressions which have been employed are used as terms of description and not of limitation and it is not intended in the use of such terms and expressions to exclude any equivalents of the features shown and described or portions thereof, since it is recognized that various modifications are possible within the scope of the invention claimed.

What is claimed is:

1. A method of treating baker's yeast comprising treating an aqueous suspension of said yeast with a sufficient amount of an acid to lower the pH of the suspension to a range of from about 0.9 to about 2 under conditions whereby the initial leavening activity of the yeast when added to sweet dough is not substantially detrimentally affected and incorporating into the acid treated yeast suspension a sufficient amount of a neutralizing agent to raise the pH of the suspension to the range of from about 2.5 to about 6, the major portion of the neutralizing agent being composed of a material which is a source of ammonium ions, thereby improving the filterability of the yeast suspension.

2. A method of treating baker's yeast as defined in claim 1, wherein the yeast after being neutralized is made into active dry yeast.

3. A method of treating baker's yeast as defined in claim 1, wherein the aqueous suspension of yeast is treated with a sufficient amount of an acid to lower the pH of the suspension to a range of from about 1.1 to about 1.5.

4. A method of treating baker's yeast as defined in claim 1, wherein the aqueous suspension of yeast is maintained at a pH of from about 0.9 to about 2 at a temperature of from about the freezing point of the yeast suspension to about 120° F for a period of from about 5 seconds to about 180 minutes.

5. A method of treating baker's yeast as defined in claim 4, wherein the aqueous suspension of yeast is maintained at a temperature of from about 40° to about 60° F for a period of from about 30 to about 60 minutes.

6. A method of treating baker's yeast as defined in claim 1, wherein the acid treated yeast suspension is neutralized to a pH of from about 3.5 to about 4.5.

7. A method of treating baker's yeast as defined in claim 4, wherein the acid treated yeast suspension is neutralized under conditions and with a sufficient amount of a source of ammonium ions to improve the rehydratability of active dry yeast prepared from such treated yeast as compared to the rehydratability of active dry yeast prepared from acid treated yeast neutralized with NaOH.

8. A method of treating baker's yeast as defined in claim 5, wherein the acid treated yeast suspension is neutralized under conditions and with a sufficient amount of a source of ammonium ions to improve the storage stability of active dry yeast prepared from such treated yeast as compared to the storage stability of active dry yeast prepared from acid treated yeast neutralized with NaOH.

9. A baker's yeast product comprising active dry yeast prepared from an aqueous suspension of yeast treated by the method defined in claim 1.

* * * * *